United States Patent
Chaudhari et al.

(10) Patent No.: US 6,420,615 B1
(45) Date of Patent: *Jul. 16, 2002

(54) PROCESS FOR THE CONVERSION OF 1,4 BUTYNEDIOL TO 1,4 BUTENEDIOL

(75) Inventors: Raghunath Vitthal Chaudhari; Chandrashekhar Vasant Rode; Rengaswamy Jaganathan; Manisha Madhukar Telkar; Vilas Hari Rane, all of Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 09/716,707

(22) Filed: Nov. 20, 2000

(51) Int. Cl.[7] .......................... C07C 31/18; C07C 27/00
(52) U.S. Cl. ........................................ 568/857; 568/861
(58) Field of Search ................................ 568/857, 861

(56) References Cited

U.S. PATENT DOCUMENTS 5,650,546 A  7/1997  Chaudhari et al. .......... 585/269
6,166,269 A  12/2000  Chaudhari et al. .......... 568/814

FOREIGN PATENT DOCUMENTS

CA  2260810  4/1998

Primary Examiner—Johann Richter
Assistant Examiner—Elvis O. Price
(74) Attorney, Agent, or Firm—Ladas & Parry

(57) ABSTRACT

A process for the preparation of 1,4 butenediol comprising hydrogenating an aqueous solution of 1,4 butynediol under stirring conditions over a supported platinum or palladium and nickel catalyst in basic medium at a temperature in the range of 20–110° C. and pressure in the range between 200–700 psig till the reaction is completed, cooling the reaction mixture to room temperature and separating the catalyst by known methods to obtain 1,4 butenediol.

7 Claims, No Drawings

PROCESS FOR THE CONVERSION OF 1,4 BUTYNEDIOL TO 1,4 BUTENEDIOL

FIELD OF THE INVENTION

The present invention relates to a process for the conversion of 1,4 butynediol to 1,4 butenediol by selective liquid phase hydrogenation. More particularly, the present invention relates to a process for the conversion of 1,4 butynediol to 1,4 butenediol in a basic medium using a novel noble metal containing catalyst.

BACKGROUND OF THE INVENTION 1,4 butenediol is a useful intermediate in the production of pesticide, insecticide and vitamin $B_6$. Being an unsaturated diol it can be used in the synthesis of many organic products such as tetrahydrofuran, n-methyl pyrrolidone, γ-butyrolactone, etc. It is also used as an additive in the paper industry, as a stabiliser in resin manufacture, as a lubricant for bearing systems and in the synthesis of allyl phosphates.

Prior art discloses the use of a number of catalysts for the manufacture of 1,4 butenediol by the hydrogenation of 1,4 butynediol. Most of the prior art patents are based on a combination of palladium with one or more mixed compounds of copper, zinc, calcium, cadmium, lead, alumina, mercury, tellurium, gallium, etc. GB A 871804 describes the selective hydrogenation of acetylinic compound in a suspension method using a Pd catalyst which has been treated with the salt solutions of Zn, Cd, Hg, Ga, Th, In, or Ga. The process is carried out at milder conditions with 97% selectivity for cis 1,2-butenediol and 3% to the trans form. Moreover, use of organic amines have been suggested as promoters in the catalyst system.

U.S. Pat. No. 2,681,938 discloses the use of a Lindlar catalyst (lead doped Pd catalyst), for the selective hydrogenation of acetylinic compounds. The drawback of this process is the use of additional amines such as pyridine to obtain good selectivity for 1,4 butenediol.

German patent DE 1, 213, 839 describes a Pd catalyst doped with Zn salts and ammonia for the partial hydrogenation of acetylinic compounds. However, this catalyst suffers from the drawback of short lifetime due to poisoning.

German patent application DE A 2, 619, 660 describes the use of $Pd/Al_2O_3$ catalyst that has been treated with carbon monoxide for the hydrogenation of butynediol in an inert solvent. The disadvantage of this catalyst is that is treated with carbon monoxide gas which is highly toxic and difficult to handle.

U.S. Pat. No. 2,961,471 discloses a Raney nickel catalyst useful for the partial hydrogenation of 1,4 butynediol. The catalyst of this process gives a low selectivity for 1,4 butenediol. Another U.S. Pat. No. 2,953,604 describes a Pd containing charcoal and copper catalyst for the reduction of 1,4 butynediol to 1,4 butenediol with 41% selectivity for 1,4 butenediol. However, this process results in the formation of a large number of side products and is therefore undesirable.

U.S. Pat. No. 4,001,344 discloses the use of palladium mixed with $γ-Al_2O_3$ along with both zinc and cadmium or either zinc or cadmium together with bismuth or tellurium at 65° C. to 72° C. and 4–12.5 bars hydrogen pressure for the preparation of 1,4 butenediol by the selective hydrogenation of 1,4 butynediol. However, a large number of residues are formed (7.5–12%) which lowers the selectivity of 1,4 butenediol to 88%.

U.S. Pat. Nos. 5,521,139 and 5,728,900 describes the use of a Pd containing catalyst for the hydrogenation of 1,4 butynediol to prepare 1,4 butenediol. The catalyst used is a fixed bed catalyst prepared by applying Pd and Pb or Pd and Cd successively by vapor deposition or sputtering to a metal gauze or a metal foil acting as a support. In this process also the selectivity obtained for cis 1,4 butenediol is 98%. The disadvantage of this process is that a trans butenediol with residues are also obtained.

All the above catalysts for the hydrogenation of butynediol to butenediol suffer from disadvantages such as they contain more than two metals along with other promoters such as organic amines. Their preparation becomes cumbersome and all the reported catalysts do not give complete selectivity for the desired product 1,4 butenediol. The formation of side products and residues have also been reported which affect the efficiency of the process and the recovery of pure 1,4 butenediol is difficult. Another disadvantage that prior art catalysts suffer from is short life due to fast deactivation.

The prior art literature shows that the catalysts used for the hydrogenation of 1,4 butynediol are mainly palladium or nickel based catalysts. There is no disclosure or report on the use of platinum based catalysts or catalysts containing a combination of palladium and nickel for the hydrogenation of 1,4 butynediol to prepare 1,4 butenediol.

It is therefore important to obtain and/or develop catalysts that overcome the disadvantages of prior art catalysts used in the hydrogenation of 1,4 butynediol to 1,4 butenediol enumerated above.

OBJECTS OF THE INVENTION

The main object of the invention is to provide a process for the preparation of 1,4 butenediol by the hydrogenation of 1,4 butynediol that is cheap and efficient.

It is another object of the invention to provide a process for the preparation of 1,4 butenediol with 100% selectivity.

It is another object of the invention to provide a process for the conversion of 1,4 butynediol to 1,4 butenediol using a noble metal catalyst that optionally contains nickel, on a suitable support, under mild reaction conditions without poisoning.

It is a further object of the invention to provide a process for the conversion of 1,4 butynediol to 1,4 butendiol that shows 100% selectivity for the production of cis 1,4 butenediol.

It is a further object of the invention to provide a process for the conversion of 1,4 butynediol to 1,4 butenediol that uses a stable catalyst that is capable of being recycled a number of times without losing its activity and selectivity.

It is another object of the invention to provide a process for the preparation of 1,4 butendiol with 100% selectivity for the production of cis 1,4 butenediol by mere separation of the catalyst.

SUMMARY OF THE INVENTION

Accordingly the present invention relates to a process for the preparation of 1,4 butenediol comprising hydrogenation of an aqueous solution of 1,4 butynediol under stirring conditions, over a supported platinum, palladium and nickel catalyst in basic medium at a temperature in the range of 20–110° C. and $H_2$ pressure in the range between 200–700 psig till the reaction is completed, cooling the reaction mixture to room temperature and separating the catalyst by known methods to obtain 1,4 butenediol.

In one embodiment of the invention, the concentration of 1,4 butynediol in aqueous medium is in the range of 10–50%.

In another embodiment of the invention, the pH of the reaction mixture is maintained in the range of 8–10 by adding a base such as ammonia.

In a further embodiment of the invention, the temperature of the reaction is preferably in the range of 30–90° C.

In yet another embodiment of the invention, the catalyst is recycled 10 times without losing its activity or selectivity and the turn over number (TON) is $4 \times 10^3 h^{-1}$.

In yet another embodiment of the invention, the catalyst is of the general formula AB(y)C(z) wherein A is a support comprising of carbonate of calcium or zeolite, B is platinum or palladium, y=0.2 to 10%, C is nickel and z=0 to 15.0%, with the proviso that when B is Pt, z=0.

DETAILED DESCRIPTION OF THE INVENTION

In the present invention the catalyst is prepared by impregnating palladium or platinum precursor with support (such as $CaCO_3$, $MgCO_3$, $BaCO_3$, or $NH_4$—ZSM 5) in a basic medium (pH=7–12), stirred in water and heated in the temperature range of 60–120° C., preferably 70–90° C. The mixture is then reduced by adding a conventional reducing agent such as formaldehyde. The solution is stirred, filtered, washed and dried at a temperature in the range of 100–250° C., preferably 140–200° C. in static air for a period in the range of 5–12 hours.

The hydrogenation catalyst used in the process of the invention is of the general formula AB(y)C(z) wherein A is a support comprising of a salt of a Group II A metal or zeolite, B is a noble metal, y=0.2 to 10%, C is nickel and z=0 to 15.0% with the proviso that when B is Pt, z=0.

The hydrogenation catalyst of the general formula AB(y)C(z) wherein A is a support comprising of a salt of a Group II A metal or zeolite, B is Pd or Pt, y=0.2 to 10%, C is nickel and z=0 to 15.0% with the proviso that when B is Pt, z=0, is prepared by:

i. dissolving a Pd or Pt precursor in a mineral acid by stirring at a temperature in the range between 60° C. to 120° C.;

ii. diluting the above solution by adding water;

iii. adjusting the pH of the solution to the range of 8–12 by adding a base;

iv. adding a support to the above solution;

v. heating the mixture to a temperature in the range of 60° C. to 120° C.;

vi. reducing the above mixture using a conventional reducing agent;

vii. separating the catalyst formed by any conventional method;

viii. washing and drying the product to obtain the said catalyst.

The catalyst may optionally have a combination of Pd with nickel. When the noble metal comprises of palladium and z=0.2 to 15%, the catalyst obtained at the end of step viii above is mixed with a solution of nickel in a basic medium having a pH in the range of 8–12, the mixture stirred for about 1 hour and the catalyst separated by any conventional method. The catalyst is then dried at about 150° C. up to 10 hours in static air, reduced at a temperature in the range of between 390–420° C. for a time period in the range of between 5–12 hours in a flow of hydrogen, the reduced catalyst is then separated by any conventional method and washed and dried to obtain the final catalyst containing palladium and nickel.

The source of Pd or Pt is a salt of Pd or Pt selected from the group consisting of acetate, bromide, and chloride and the source of nickel is a salt of nickel selected from the group consisting of acetate, carbonate, chloride and nitrate.

The support is a Group II A metal salt selected from the group consisting of acetates, nitrates, chlorides and carbonates of magnesium, calcium and barium and the source of zeolite is $NH_4$—ZSM5.

The base used may be selected from the group consisting of sodium carbonate, potassium carbonate, potassium hydroxide, and sodium hydroxide.

The reducing agent used in the preparation of the catalyst is selected from the group consisting of hydrazine hydrate, hydrogen containing gas, and formaldehyde.

The catalyst prepared as per the procedure described below in the examples can be reduced in a muffle furnace at 400° C. in hydrogen flow for a time period ranging between 5–12 hours, preferably 7 hours.

In a feature of the invention, high purity 1,4 butenediol can be simply obtained by the removal of the catalyst from the product stream. The selectivity of the process at milder process conditions is 100%.

The present invention achieves 100% conversion of 1,4 butynediol with 100% selectivity for cis 1,4 butenediol at mild process conditions. At higher temperatures, while 1,4 butynediol is converted completely, the selectivity for cis 1,4 butenediol is less, generally $\leq 90\%$. The formation of side products such as acetals, γ-hydroxybutaraldehyde, butanol at higher temperatures is also more pronounced.

Hydrogenation of 1,4 butynediol is carried out in an autoclave under stirring conditions in the presence of a Pd or Pt containing catalyst suspended in a mixture of 1,4 butynediol in water at temperature and pressure conditions as given in the examples. The mixture is made alkaline (pH=8–12), by the addition of base such as ammonia. Before pressurising the autoclave, it is ensured that there is no air present inside the autoclave. The hydrogenation is complete when the absorption of hydrogen is stopped or unchanged. After the reaction is complete, the reactor is cooled to ambient temperature and the contents discharged and analysed using a gas chromatograph.

The present invention is described below by way of examples. However, the following examples are illustrative and should not be construed as limiting the scope of the invention.

EXAMPLE 1

Preparation of Pd Supported Catalyst

The catalyst is prepared by impregnating palladium precursor such as palladium chloride $PdCl_2$ with a support (such as $CaCO_3$, $MgCO_3$, $BaCO_3$, or $NH_4$—ZSM 5) in basic medium, stirred in water and heated at 80° C. The mixture is then reduced by adding formaldehyde. The solution is stirred, filtered, washed and dried at 150° C. for 10 hours.

EXAMPLE 2

Preparation of Pt Supported Catalyst

The catalyst is prepared by impregnating platinum precursor such as platinum chloride with a support (such as $CaCO_3$, $MgCO_3$, $BaCO_3$, or $NH_4$—ZSM 5) in basic medium, stirred in water and is heated at 80° C. The mixture is then reduced by adding formaldehyde. The solution is stirred, filtered, washed and dried at 150° C. for 10 hours.

EXAMPLE 3

Performance of 1% Pd/MgCO$_3$ Catalyst in the Hydrogenation of 1,4 Butynediol to 1,4 Butenediol This example illustrates the performance of 1% Pd/MgCO$_3$ catalyst in the hydrogenation of 1,4 butynediol to 1,4 butenediol The catalyst is prepared by impregnating palladium precursor PdCl$_2$ with MgCO$_3$ support in basic medium, stirred in water and is heated at 80° C. The mixture is then reduced by adding formaldehyde. The solution is stirred, filtered, washed and dried at 150° C. for 10 hours.

The reaction in the presence of this catalyst was carried out in an autoclave according to the procedure described hereinabove.

| The reaction was carried out at the following reaction conditions: | |
| --- | --- |
| Concentration of 1,4 butynediol in water | 20% |
| Weight of catalyst | 0.13 gms |
| Temperature | 50° C. |
| H$_2$ pressure | 350 psig |
| The following results are obtained: | |
| Conversion of 1,4 butynediol | 100% |
| Selectivity for cis 1,4 butenediol | 99.8% |

EXAMPLE 4

Performance of 1% Pd/CaCO$_3$ Catalyst in the Hydrogenation of 1,4 Butynediol to 1,4 Butenediol This example illustrates the performance of 1% Pd/CaCO$_3$ catalyst in the hydrogenation of 1,4 butynediol to 1,4 butenediol The catalyst is prepared by impregnating palladium precursor PdCl$_2$ with CaCO$_3$ support in basic medium, stirred in water and is heated at 80° C. The mixture is then reduced by adding formaldehyde. The solution is stirred, filtered, washed and dried at 150° C. for 10 hours.

The hydrogenation reaction in the presence of this catalyst was carried out in an autoclave according to the procedure described above.

| The reaction was carried out at the following reaction conditions: | |
| --- | --- |
| Concentration of 1,4 butynediol in water | 20% |
| Weight of catalyst | 0.13 gms |
| Temperature | 50° C. |
| H$_2$ pressure | 350 psig |
| The following results are obtained: | |
| Conversion of 1,4 butynediol | 100% |
| Selectivity for cis 1,4 butenediol | 98.2% |

EXAMPLE 5

Performance or Use of Recycling the 1% Pd/CaCO$_3$ Catalyst Ten Times in the Hydrogenation of 1,4 Butynediol to 1,4 Butenediol This example illustrates the performance or use of recycling of 1% Pd/CaCO$_3$ catalyst ten times in the hydrogenation of 1,4 butynediol to 1,4 butenediol The reaction in the presence of this catalyst was carried out in an autoclave according to the procedure described above.

| The reaction was carried out at the following reaction conditions: | |
| --- | --- |
| Catalyst | 1% Pd/CaCO$_3$ |
| Weight of catalyst | 1.0 gms |
| Grams of 1,4 butynediol converted | 2191 |
| Temperature | 50° C. |
| H$_2$ pressure | 350 psig |
| The following results are obtained: | |
| Conversion of 1,4 butynediol | 100% |
| Selectivity for cis 1,4 butenediol | 98% |
| TON | 4 × 10$^3$h$^{-1}$ |

EXAMPLE 6

Performance of 1%Pd/BaCO$_3$ Catalyst in the Hydrogenation of 1,4 Butynediol to 1,4 Butenediol This example illustrates the performance of 1% Pd/BaCO$_3$ catalyst in the hydrogenation of 1,4 butynediol to 1,4 butenediol The catalyst is prepared by impregnating palladium precursor PdCl$_2$ with BaCO$_3$ support in basic medium, stirred in water and is heated at 80° C. The mixture is then reduced by adding formaldehyde. The solution is stirred, filtered, washed and dried at 150° C. for 10 hours.

The reaction in the presence of this catalyst was carried out in an autoclave according to the procedure described above.

| The reaction was carried out at the following reaction conditions: | |
| --- | --- |
| Concentration of 1,4 butynediol in water | 10% |
| Weight of catalyst | 0.065 gms |
| Temperature | 50° C. |
| H$_2$ pressure | 350 psig |
| The following results are obtained: | |
| Conversion of 1,4 butynediol | 100% |
| Selectivity for cis 1,4 butenediol | 100% |

EXAMPLE 7

| The reaction was carried out at the following reaction conditions: | |
| --- | --- |
| Catalyst | 1% Pd/BaCO$_3$ |
| Weight of catalyst | 0.13 gms |
| Concentration of 1,4 butynediol in water | 20% |
| Temperature | 50° C. |
| H$_2$ pressure | 350 psig |
| The following results are obtained: | |
| Conversion of 1,4 butynediol | 100% |
| Selectivity for cis 1,4 butenediol | 100% |

EXAMPLE 8

| The reaction was carried out at the following reaction conditions: | |
|---|---|
| Catalyst | 1% Pd/BaCO$_3$ |
| Weight of catalyst | 0.13 gms |
| Concentration of 1,4 butynediol in water | 20% |
| Temperature | 50° C. |
| H$_2$ pressure | 500 psig |
| The following results are obtained: | |
| Conversion of 1,4 butynediol | 100% |
| Selectivity for cis 1,4 butenediol | 100% |

EXAMPLE 9

| The reaction was carried out at the following reaction conditions: | |
|---|---|
| Catalyst | 1% Pd/BaCO$_3$ |
| Weight of catalyst | 0.13 gms |
| Concentration of 1,4 butynediol in water | 20% |
| Temperature | 80° C. |
| H$_2$ pressure | 350 psig |
| The following results are obtained: | |
| Conversion of 1,4 butynediol | 100% |
| Selectivity for cis 1,4 butenediol | 95.2% |
| Side products | 4.8% |

EXAMPLE 10

| The reaction was carried out at the following reaction conditions: | |
|---|---|
| Catalyst | 1% Pd/BaCO$_3$ |
| Weight of catalyst | 0.13 gms |
| Concentration of 1,4 butynediol in water | 20% |
| Temperature | 80° C. |
| H$_2$ pressure | 500 psig |
| The following results are obtained: | |
| Conversion of 1,4 butynediol | 100% |
| Selectivity for cis 1,4 butenediol | 94.5% |
| Side Products | 5.5% |

EXAMPLE 11

| The reaction was carried out at the following reaction conditions: | |
|---|---|
| Catalyst | 1% Pd/BaCO$_3$ |
| Weight of catalyst | 0.23 gms |
| Concentration of 1,4 butynediol in water | 35% |
| Temperature | 50° C. |
| H$_2$ pressure | 350 psig |
| The following results are obtained: | |
| Conversion of 1,4 butynediol | 100% |
| Selectivity for cis 1,4 butenediol | 100% |

EXAMPLE 12

| The reaction was carried out at the following reaction conditions: | |
|---|---|
| Catalyst | 1% Pd/BaCO$_3$ |
| Weight of catalyst | 0.46 gms |
| Concentration of 1,4 butynediol in water | 70% |
| Temperature | 50° C. |
| H$_2$ pressure | 350 psig |
| The following results are obtained: | |
| Conversion of 1,4 butynediol | 100% |
| Selectivity for cis 1,4 butenediol | 82.1% |

EXAMPLE 13

This example illustrates the performance or use of 1% Pd/NH$_4$—ZSM 5 catalyst in the hydrogenation of 1,4 butynediol to 1,4 butenediol The catalyst is prepared by impregnating palladium precursor with NH$_4$—ZSM 5 support in basic medium, stirred in water and is heated at 80° C. The mixture is then reduced by adding formaldehyde. The solution is stirred, filtered, washed and dried at 150° C. for 10 hours.

The hydrogenation reaction in the presence of this catalyst was carried out in an autoclave according to the procedure described above.

| The reaction was carried out at the following reaction conditions: | |
|---|---|
| Concentration of 1,4 butynediol in water | 20% |
| Weight of catalyst | 0.13 gms |
| Temperature | 50° C. |
| H$_2$ pressure | 350 psig |
| The following results are obtained: | |
| Conversion of 1,4 butynediol | 100% |
| Selectivity for cis 1,4 butenediol | 100% |

EXAMPLE 14

This example illustrates the performance or use of 10% Ni-1% Pd/CaCO$_3$ catalyst in the hydrogenation of 1,4 butynediol to 1,4 butenediol The catalyst is prepared by impregnating palladium precursor with CaCO$_3$ support in basic medium, stirred in water and is heated at 80° C. The mixture is then reduced by adding formaldehyde. The solution is stirred, filtered, washed and dried at 150° C. for 10 hours. Then the solution of nickel nitrate is stirred with 1% Pd/CaCO$_3$ catalyst in basic medium, filtered, dried and then reduced at 500° C. in the flow of hydrogen.

The reaction in the presence of this catalyst was carried out in an autoclave according to the procedure described above.

| The reaction was carried out at the following reaction conditions: | |
|---|---|
| Concentration of 1,4 butynediol in water | 20% |
| Weight of catalyst | 0.13 gms |

EXAMPLE 15

This example illustrates the performance or the use of 1% Pt/MgCO$_3$ catalyst in the hydrogenation of 1,4 butynediol to 1,4 butenediol.

The catalyst is prepared by impregnating platinum precursor PtCl$_2$ with MgCO$_3$ support in basic medium, stirred in water and is heated at 80° C. The mixture is then reduced by adding formaldehyde. The solution is stirred, filtered, washed and dried at 150° C. for 10 hours.

The hydrogenation reaction in the presence of this catalyst was carried out in an autoclave according to the procedure described above.

| The reaction was carried out at the following reaction conditions: | |
|---|---|
| Concentration of 1,4 butynediol in water | 20% |
| Weight of catalyst | 0.13 gms |
| Temperature | 50° C. |
| H$_2$ pressure | 350 psig |
| The following results are obtained: | |
| Conversion of 1,4 butynediol | 100% |
| Selectivity for cis 1,4 butenediol | 99.8% |

EXAMPLE 16

This example illustrates the performance or the use of 1% Pt/CaCO$_3$ catalyst in the hydrogenation of 1,4 butynediol to 1,4 butenediol The catalyst is prepared by impregnating platinum precursor PtCl$_2$ with CaCO$_3$ support in basic medium, stirred in water and is heated at 80° C. The mixture is then reduced by adding formaldehyde. The solution is stirred, filtered, washed and dried at 150° C. for 10 hours.

The hydrogenation reaction in the presence of this catalyst was carried out in an autoclave according to the procedure described above.

| The reaction was carried out at the following reaction conditions: | |
|---|---|
| Concentration of 1,4 butynediol in water | 10% |
| Weight of catalyst | 0.065 gms |
| Temperature | 50° C. |
| H$_2$ pressure | 350 psig |
| The following results are obtained: | |
| Conversion of 1,4 butynediol | 100% |
| Selectivity for cis 1,4 butenediol | 100% |

EXAMPLE 17

| The reaction was carried out at the following reaction conditions: | |
|---|---|
| Catalyst | 1% Pt/CaCO$_3$ |
| Weight of catalyst | 0.13 gms |
| Concentration of 1,4 butynediol in water | 20% |
| Temperature | 50° C. |
| H$_2$ pressure | 350 psig |
| The following results are obtained: | |
| Conversion of 1,4 butynediol | 100% |
| Selectivity for cis 1,4 butenediol | 100% |

EXAMPLE 18

| The reaction was carried out at the following reaction conditions: | |
|---|---|
| Catalyst | 1% Pt/CaCO$_3$ |
| Weight of catalyst | 0.13 gms |
| Concentration of 1,4 butynediol in water | 20% |
| Temperature | 50° C. |
| H$_2$ pressure | 500 psig |
| The following results are obtained: | |
| Conversion of 1,4 butynediol | 100% |
| Selectivity for cis 1,4 butenediol | 100% |

EXAMPLE 19

| The reaction was carried out at the following reaction conditions: | |
|---|---|
| Catalyst | 1% Pt/CaCO$_3$ |
| Weight of catalyst | 0.13 gms |
| Concentration of 1,4 butynediol in water | 20% |
| Temperature | 80° C. |
| H$_2$ pressure | 350 psig |
| The following results are obtained: | |
| Conversion of 1,4 butynediol | 100% |
| Selectivity for cis 1,4 butenediol | 97.2% |
| Side products | 2.8% |

EXAMPLE 20

| The reaction was carried out at the following reaction conditions: | |
|---|---|
| Catalyst | 1% Pt/CaCO$_3$ |
| Weight of catalyst | 0.13 gms |
| Concentration of 1,4 butynediol in water | 20 % |
| Temperature | 80° C. |
| H$_2$ pressure | 500 psig |
| The following results are obtained: | |
| Conversion of 1,4 butynediol | 100% |
| Selectivity for cis 1,4 butenediol | 95.7% |
| Side Products | 4.3% |

—continued

| Temperature | 50° C. |
|---|---|
| H$_2$ pressure | 350 psig |
| The following results are obtained: | |
| Conversion of 1,4 butynediol | 100% |
| Selectivity for cis 1,4 butenediol | 100% |

EXAMPLE 21

| The reaction was carried out at the following reaction conditions: | |
|---|---|
| Catalyst | 1% Pt/CaCO$_3$ |
| Weight of catalyst | 0.23 gms |
| Concentration of 1,4 butynediol in water | 35% |
| Temperature | 50° C. |
| H$_2$ pressure | 350 psig |
| The following results are obtained: | |
| Conversion of 1,4 butynediol | 100% |
| Selectivity for cis 1,4 butenediol | 100% |

EXAMPLE 22

| The reaction was carried out at the following reaction conditions: | |
|---|---|
| Catalyst | 1% Pt/CaCO$_3$ |
| Weight of catalyst | 0.46 gms |
| Concentration of 1,4 butynediol in water | 70% |
| Temperature | 50° C. |
| H$_2$ pressure | 350 psig |
| The following results are obtained: | |
| Conversion of 1,4 butynediol | 100% |
| Selectivity for cis 1,4 butenediol | 83.4% |

EXAMPLE 23

This example illustrates the performance of 1% Pt/BaCO$_3$ catalyst in the hydrogenation of 1,4 butynediol to 1,4 butenediol The catalyst is prepared by impregnating platinum precursor PtCl$_2$ with BaCO$_3$ support in basic medium, stirred in water and is heated at 80° C. The mixture is then reduced by adding formaldehyde. The solution is stirred, filtered, washed and dried at 150° C. for 10 hours.

The reaction in the presence of this catalyst was carried out in an autoclave according to the procedure described above.

| The reaction was carried out at the following reaction conditions: | |
|---|---|
| Concentration of 1,4 butynediol in water | 20% |
| Weight of catalyst | 0.13 gms |
| Temperature | 50° C. |
| H$_2$ pressure | 350 psig |
| The following results are obtained: | |
| Conversion of 1,4 butynediol | 100% |
| Selectivity for cis 1,4 butenediol | 99.9% |

ADVANTAGES OF THE INVENTION

1. Selective hydrogenation of 1,4 butynediol to 1,4 butenediol is achieved using a novel 1% Pt/MgCO$_3$, 1% Pt/CaCO$_3$, 1% Pt/BaCO$_3$, 1% Pd/MgCO$_3$, 1% Pd/CaCO$_3$, 1% Pd/BaCO$_3$, 1% Pd/NH$_4$ZSM-5 and 10% Ni-1% Pd/CaCO$_3$ catalyst without any poisoning.
2. Substantially complete conversion of 1,4 butynediol to 1,4 butenediol with almost 100% selectivity to cis 1,4 butenediol is obtained at milder process conditions.
3. The separation of the product 1,4 butenediol in pure form is achieved easily by the removal of the catalyst from the reaction mixture.

We claim:

1. A process for the preparation of 1,4 butenediol comprising hydrogenating an aqueous solution of 1,4 butynediol under stirring conditions over a supported platinum or palladium and nickel catalyst in basic medium at a temperature in the range of 20–110° C. and pressure in the range between 200–700 psig till the reaction is completed, cooling the reaction mixture to room temperature and separating the catalyst by known methods to obtain 1,4 butenediol.

2. A process as claimed in claim 1 wherein the concentration of 1,4 butynediol in aqueous medium is in the range of 10–50%.

3. A process as claimed in claim 1 wherein the pH of the reaction mixture is maintained in the range of 8–10 by adding a base.

4. A process as claimed in claim 3 wherein the base is ammonia.

5. A process as claimed in claim 1 wherein the temperature of the reaction is in the range of 30–90° C.

6. A process as claimed in claim 1 wherein the catalyst is recycled 10 times without losing its activity and selectivity with the turn over number (TON) being $4 \times 10^3 h^{-1}$.

7. A process as claimed in claim 1 wherein the catalyst used is of the general formula AB(y)C(z) wherein A is a support comprising of carbonate of calcium or zeolite, B is platinum or palladium, y=0.2 to 10%, C is nickel and z=0 to 15.0% with the proviso that when B is Pt, z=0.

* * * * *